(12) United States Patent  
Zhang

(10) Patent No.: US 12,426,701 B1
(45) Date of Patent: Sep. 30, 2025

(54) WAND APPLICATOR WITH RELEASABLE SWAB HEAD

(71) Applicant: ZHUHAI DING RONG PLASTIC PRODUCTS CO., LTD., Zhuhai (CN)

(72) Inventor: Hui-Hui Zhang, Zhuhai (CN)

( * ) Notice: Subject to any disclaimer, the term of this patent is extended or adjusted under 35 U.S.C. 154(b) by 0 days.

(21) Appl. No.: 18/980,059

(22) Filed: Dec. 13, 2024

(51) Int. Cl.
| | |
|---|---|
| *A46B 9/00* | (2006.01) |
| *A45D 34/04* | (2006.01) |
| *A45D 40/26* | (2006.01) |
| *A46B 3/08* | (2006.01) |
| *A46B 11/00* | (2006.01) |
| *A61M 35/00* | (2006.01) |
| *B65D 51/32* | (2006.01) |

(52) U.S. Cl.
CPC ............ *A46B 9/005* (2013.01); *A45D 34/045* (2013.01); *B65D 51/32* (2013.01); *A45D 2200/1018* (2013.01); *A46B 3/08* (2013.01); *A46B 11/00* (2013.01); *A46B 2200/1046* (2013.01); *A61M 35/00* (2013.01)

(58) Field of Classification Search
CPC . A46B 9/005; A46B 11/00; A46B 2200/1046; A46B 3/005; A46B 3/08; A45D 34/045; A45D 2200/1018; A45D 40/265; A45D 2200/1009; B65D 51/32; A61M 35/00; A61M 35/003

USPC .......................... 401/130; 15/428, 431; 604/1
See application file for complete search history.

(56) References Cited

U.S. PATENT DOCUMENTS

| | | | | |
|---|---|---|---|---|
| 5,120,301 A | * | 6/1992 | Wu ...................... | A61M 35/006 604/3 |
| 5,364,792 A | * | 11/1994 | Stone ...................... | G01N 21/78 436/80 |
| 11,771,200 B2 | * | 10/2023 | Gauttier ............... | A45D 40/264 132/320 |

* cited by examiner

*Primary Examiner* — David J Walczak

(57) ABSTRACT

A wand applicator includes a shaft including a positioning member at a first end; a positioning hole in the positioning member, the positioning hole including an annular recess on a surface, the annular recess having a latching surface; a connection member secured to the positioning hole and including an axial hole; a ring-shaped projection at a first end, the ring-shaped projection engaged with an end of positioning member; and an annular flange on an outer surface secured to the annular recess, the annular flange including an urging surface on a first end secured to the latching surface and an inclined surface on an opposite second end; and a swab head passing through the axial hole and including an annular protrusion on a bottom, the annular protrusion extending outward from an end opposite to the ring-shaped projection.

7 Claims, 6 Drawing Sheets

WAND APPLICATOR WITH RELEASABLE SWAB HEAD

FIELD OF THE INVENTION

The invention relates to cosmetic tools and more particularly to a wand applicator including a releasable swab head having improved characteristics.

BACKGROUND OF THE INVENTION

Conventionally, a wand applicator comprises a shaft and a sponge swab head secured to one end of the shaft by adhesive. An axial hole is driven in the swab head. The shaft is inserted in the axial hole to secure to the swab head.

The conventional swab head and the shaft are secured together by adhesive. However, this has a number of disadvantages including being not environmentally friendly, the swab head being liable to dislodgement or displacement due to deterioration of the adhesive caused by certain chemical compositions (e.g., cosmetic fluid) reaction with the adhesive, a decreased tensile strength because the shaft and the swab head are secured together by adhesive, damaged structure because the swab head has the axial hole, and being not durable.

Thus, the need for improvement still exists.

SUMMARY OF THE INVENTION

It is therefore one object of the invention to provide a wand applicator comprising a shaft comprising a positioning member at a first end; a positioning hole in the positioning member, the positioning hole including an annular recess on a surface, the annular recess having a latching surface on a surface; a connection member secured to the positioning hole and comprising an axial hole; a ring-shaped projection on an edge of a first end, the ring-shaped projection engaged with an end of positioning member; and an annular flange on an outer surface, the annular flange including an urging surface on a first end and an inclined surface on an opposite second end wherein the annular flange is secured to the annular recess and the urging surface is secured to the latching surface; and a swab head passing through the axial hole of the connection member and comprising an annular protrusion on a bottom, the annular protrusion extending outward from an end opposite to the ring-shaped projection.

The invention has the following advantages and benefits in comparison with the conventional art:

Environmentally friendly and durable: the intermediate connection member is secured to the shaft and the swab head by snapping rather than by adhesive. In addition to being environmentally friendly, it also increases the tensile strength. Further, the swab head is not liable to dislodgement or displacement due to deterioration of the adhesive caused by certain chemical compositions (e.g., cosmetic fluid) reaction with the adhesive. Furthermore, the swab head does not have an axial hole as in the conventional one and thus its structure remains intact, Finally, the swab head is durable.

Quick positioning and sure snapping: Since the annular flange has an inverted hook shaped longitudinal section, when the connection member is snapped into the positioning hole of the shaft, the provision of the inclined surface facilitates the connection member to secure to the positioning hole. At this time, the urging surface urges against the latching surface so that the connection member is not easily separated from the positioning hole. This achieves the effect of quick positioning and sure snapping.

The above and other objects, features and advantages of the invention will become apparent from the following detailed description taken with the accompanying drawings.

DETAILED DESCRIPTION OF THE INVENTION

Figure 1:
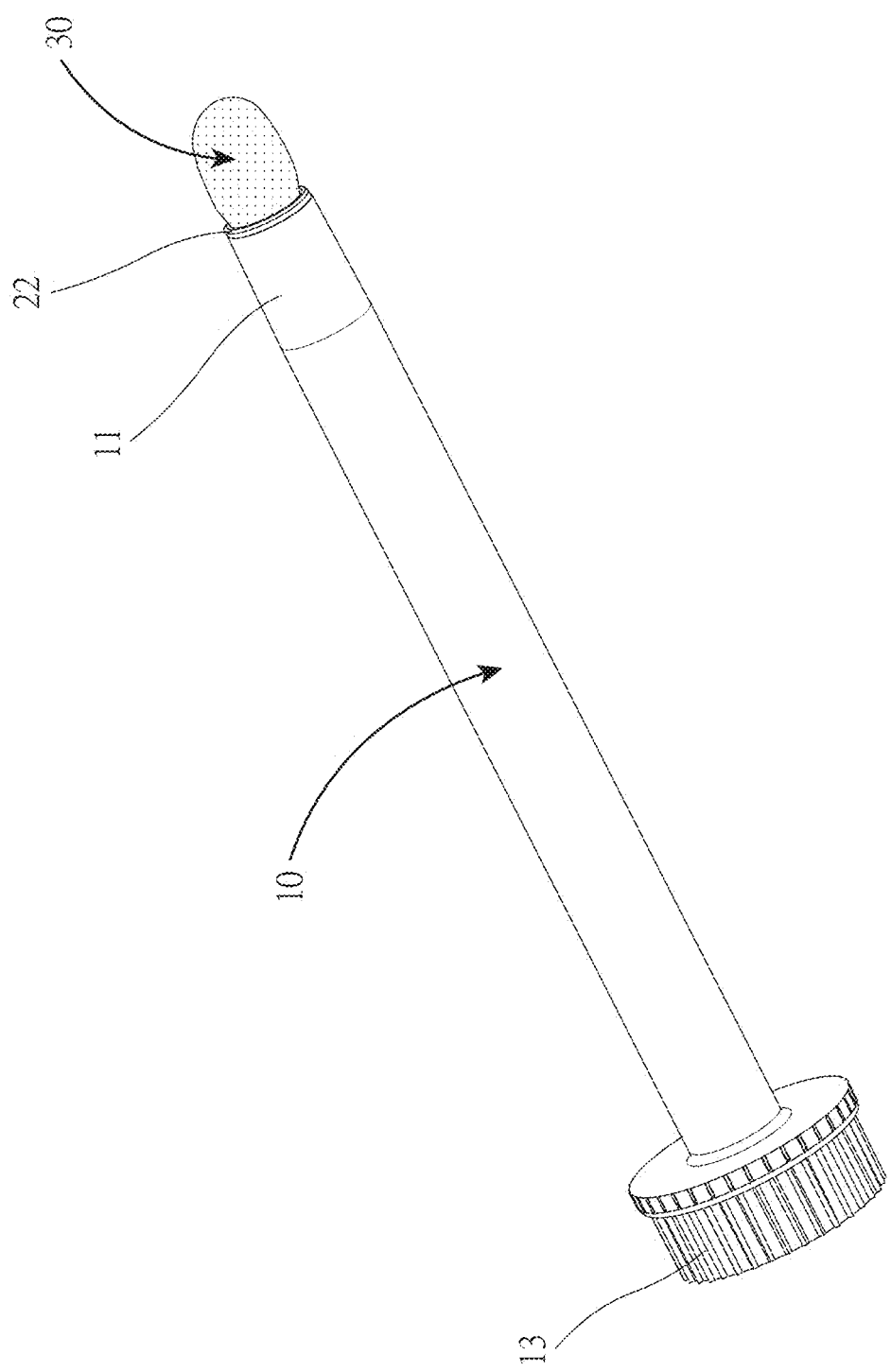
FIG. 1 is a perspective view of a wand applicator according to a first preferred embodiment of the invention.

Referring to FIGS. 1 to 4, a wand applicator 100 in accordance with a first preferred embodiment of the invention comprises the following components as discussed in detail below.

A shaft 10 comprises a positioning member 11 at a first end; a positioning hole 12 in the positioning member 11, the positioning hole 12 including an annular recess 121 on a surface, the annular recess 121 having a latching surface 1211 on a surface, and a cavity 122 on a bottom of the positioning hole 12; and an attaching member 13 at a second end opposite to the first end.

A connection member 20 is secured to the positioning hole 12. The connection member 20 comprises an axial hole 21; a ring-shaped projection 22 on an edge of a first end, the ring-shaped projection 22 engaged with an end of positioning member 11; and an annular flange 23 on an outer surface, the annular flange 23 having an inverted hook shaped longitudinal section, the annular flange 23 including an urging surface 231 on a first end and an inclined surface 232 on an opposite second end. The annular flange 23 is secured to the annular recess 121. The urging surface 231 is secured to the latching surface 1211.

A swab head 30, in the first embodiment, is implemented as a nitrile butadiene rubber (NBR) sponge and is not limited to such in other embodiments. The swab head 30 passes through the axial hole 21 of the connection member 20 to partially dispose in the shaft 10. The swab head 30 comprises an annular protrusion 31 on a bottom. The annular protrusion 31 extends outward from an end opposite to the ring-shaped projection 22 and is partially disposed in the cavity 122.

A diameter of the annular protrusion 31 is greater than that of the axial hole 21 so as to prevent the swab head 30 from being disengaged from the connection member 20.

The swab head 30 can be shaped as a sphere, an ellipsoid, or a raindrop but not limited to such. In the embodiment, the swab head 30 is shaped as a raindrop.

Figure 5:
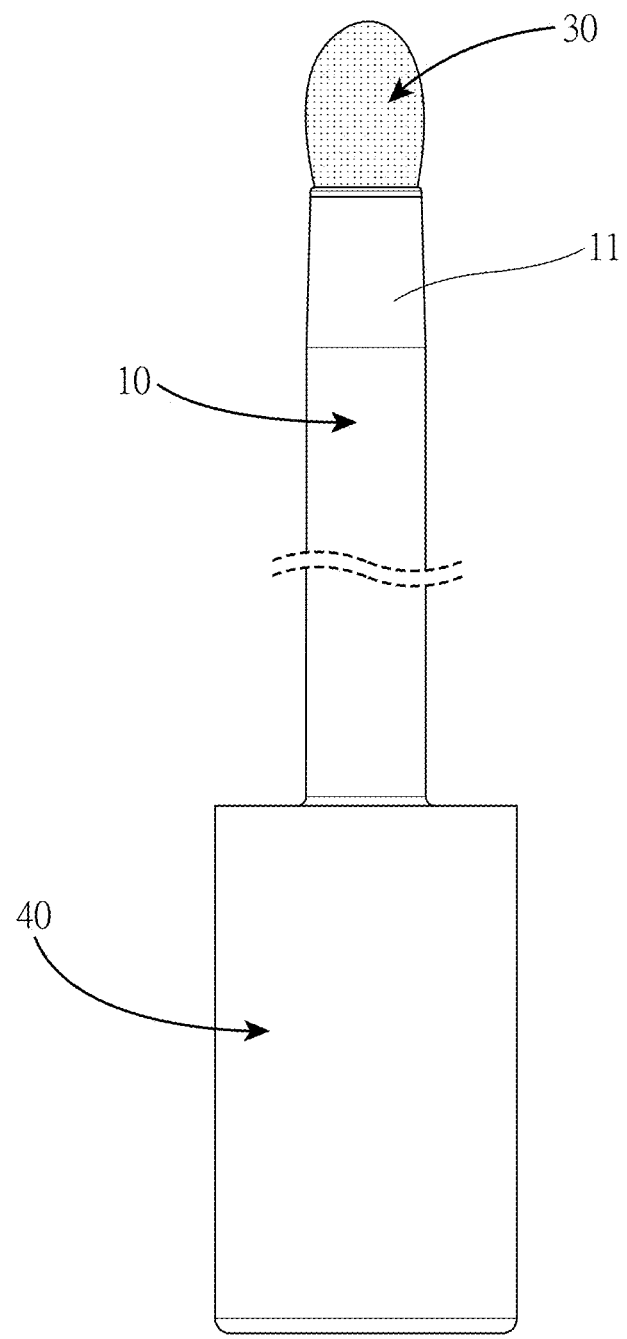
FIG. 5 is a side elevation of the wand applicator with a cap disposed on the attaching member.

Referring to FIG. 5 in conjunction with FIG. 1, the wand applicator 100 and a cap 40 of a cosmetic container together are used as one. The attaching member 13 of the shaft 10 is disposed in the cap 40. In use, an individual may use one hand to hold the cap 40 and apply the swab head 30 to desired portions of the face.

Figure 2:
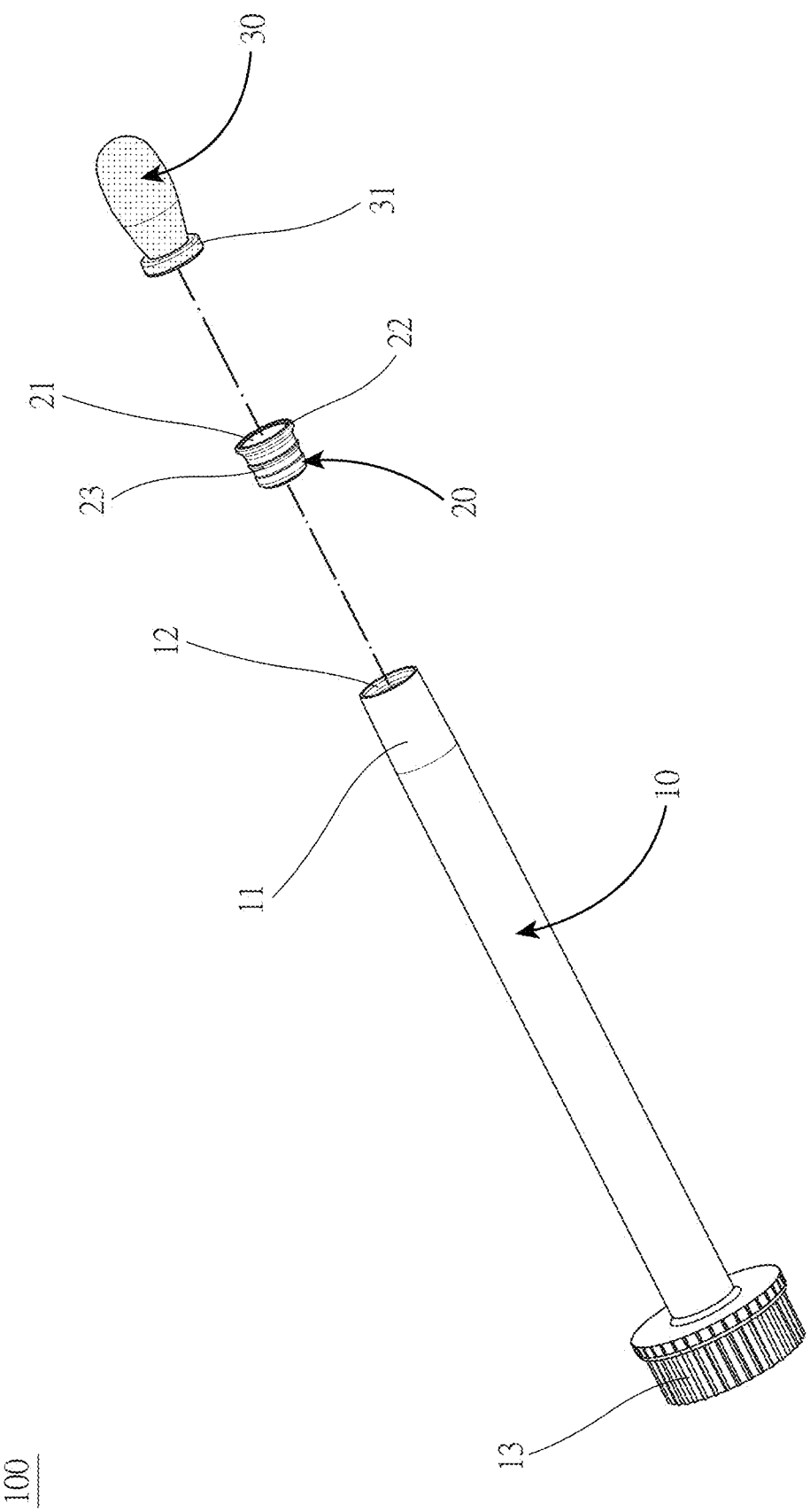
FIG. 2 is an exploded view of the wand applicator.

As shown in FIG. 2 specifically, the connection member 20 is used to fasten the shaft 10 and the swab head 30 together by snapping rather than by adhesive. This has the advantages of being environmentally friendly, increased tensile strength, and preventing the swab head 30 from being dislodged due to deterioration of the adhesive caused by certain chemical compositions (e.g., cosmetic fluid) reaction with the adhesive. Moreover, the swab head 30 does not have an axial hole 21 as in the conventional swab head 30 and thus its structure remains intact, Therefore, the swab head 30 is durable.

It is noted that the swab head 30 has good softness and flexibility because it is made of NBR sponge. After use, any cosmetics remaining on the swab head 30 can be washed away. The swab head 30 can be returned to its original shape after being deformed by pressing. There is no dirt remaining on it. It can be reused.

Figure 3:
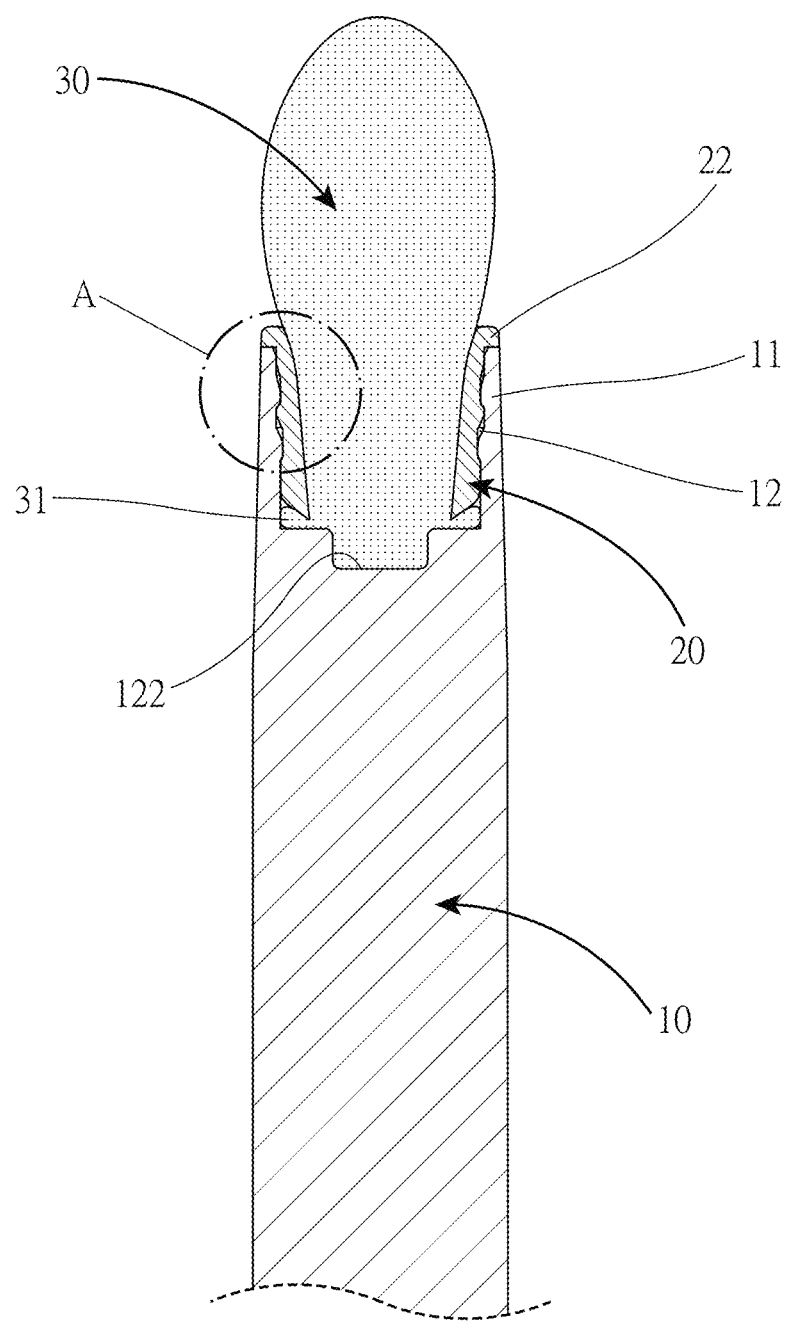
FIG. 3 is a longitudinal sectional view of the wand applicator except the attaching member.
Figure 4:
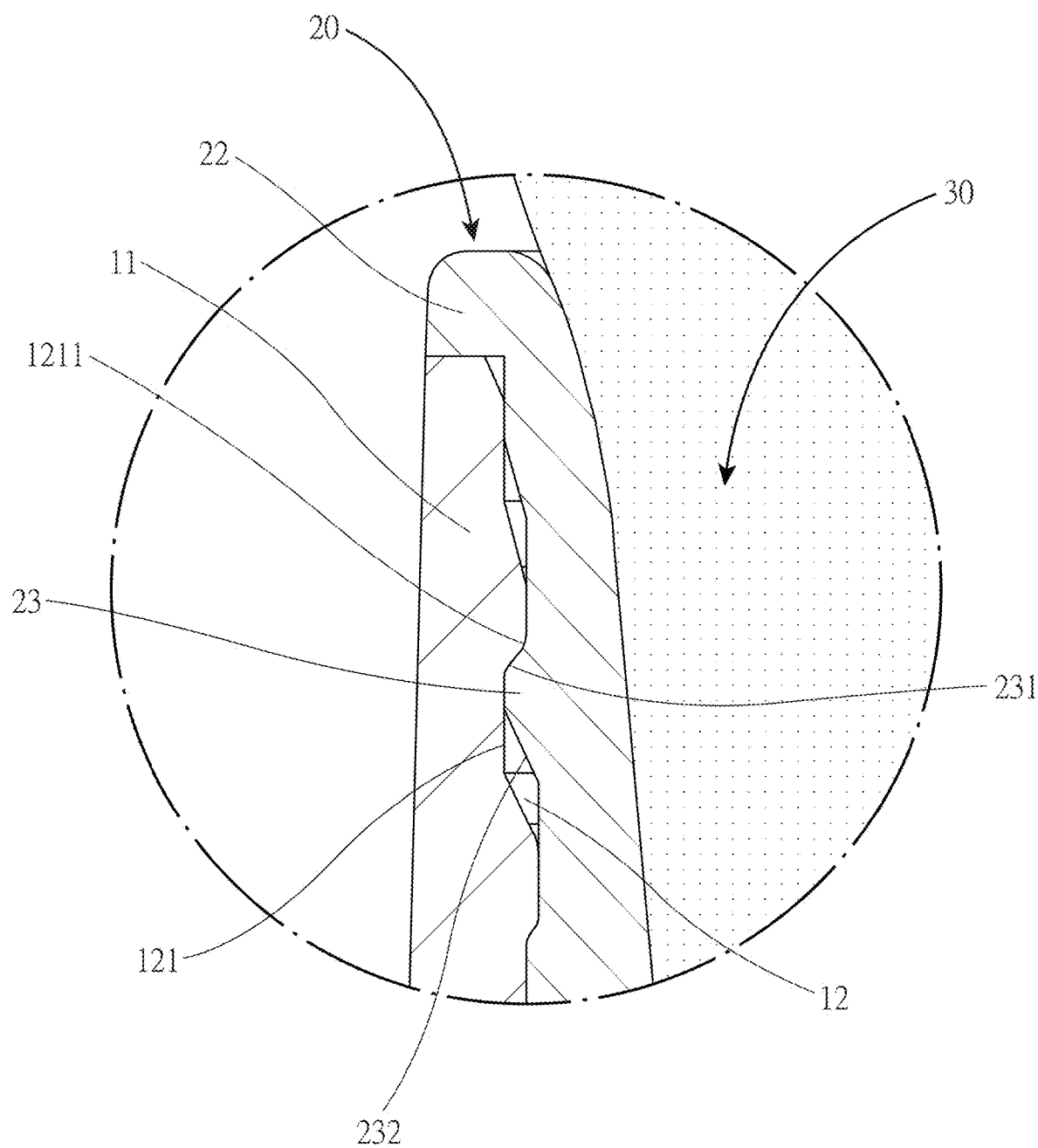
FIG. 4 is an enlarged view of the area in circle A of FIG. 3.

As shown in FIGS. 3 and 4 specifically, the annular flange 23 has the inverted hook shaped longitudinal section. When the connection member 20 is snapped in the positioning hole 12 of the shaft 10, the provision of the inclined surface 232 facilitates the connection member 20 to be secured to the positioning hole 12. Further, the urging surface 231 urges against the latching surface 1211, thereby securing the connection member 20 to the positioning hole 12. This snap fastening is quick and reliable.

Figure 6:
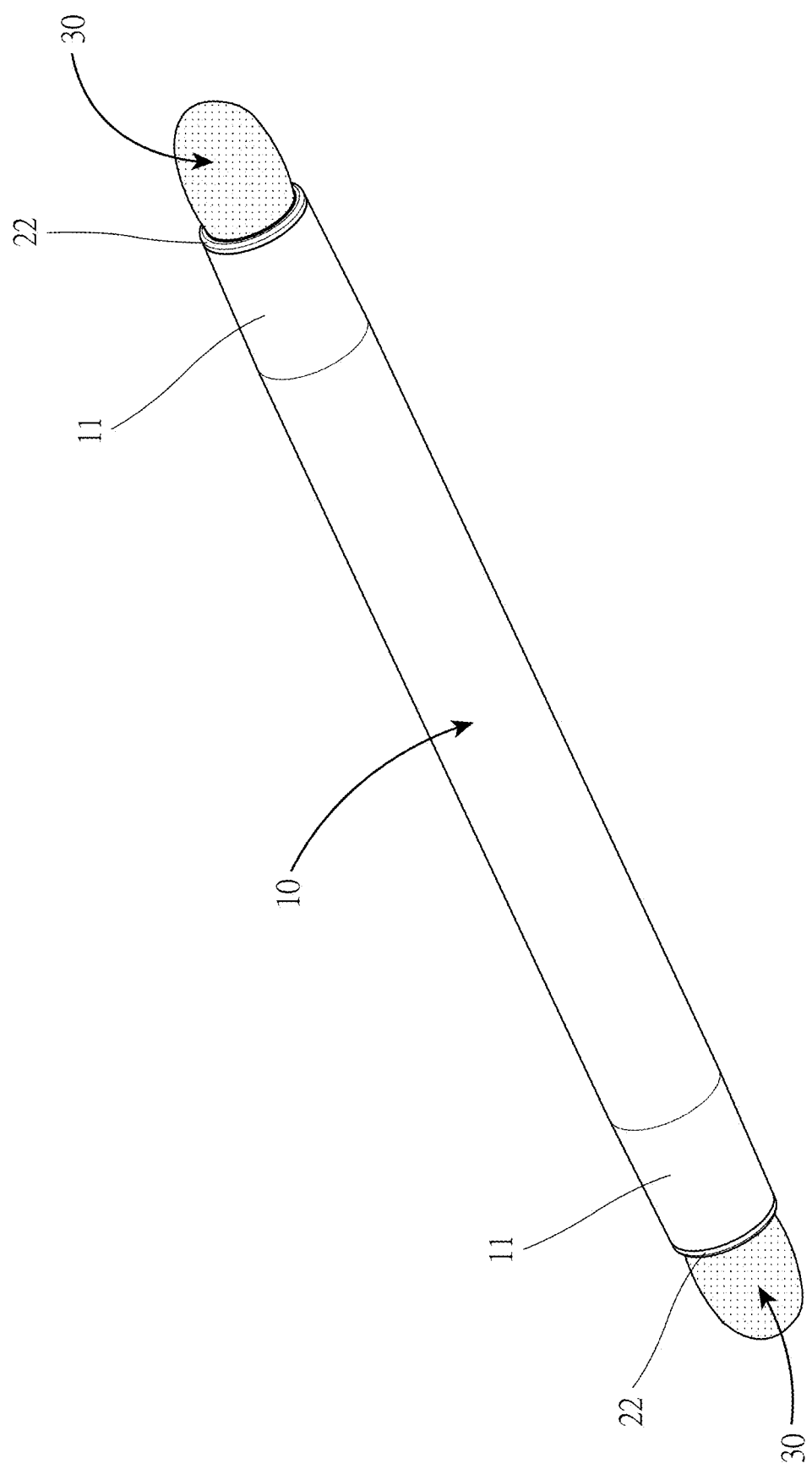
FIG. 6 is a perspective view of a wand applicator according to a second preferred embodiment of the invention.

Referring to FIG. 6, a wand applicator 100 in accordance with a second preferred embodiment of the invention is shown. The characteristics of the second preferred embodiment are substantially the same as that of the first preferred embodiment except the following: the second end of the shaft 10 is provided with the positioning member 11 rather than the attaching member 13. One swab head 30 and one connection member 20 are provided at the first end of the shaft 10 and the other swab head 30 and the other connection member 20 are provided at the second end of the shaft 10. This embodiment has increased applications.

While the invention has been described in terms of preferred embodiments, those skilled in the art will recognize that the invention can be practiced with modifications within the spirit and scope of the appended claims.

What is claimed is:

1. A wand applicator, comprising:
 a shaft comprising a positioning member at a first end; a positioning hole in the positioning member, the positioning hole including an annular recess on a surface, the annular recess having a latching surface on a surface;
 a connection member secured to the positioning hole and comprising an axial hole; a ring-shaped projection on an edge of a first end, the ring-shaped projection engaged with an end of positioning member; and an annular flange on an outer surface, the annular flange including an urging surface on a first end and an inclined surface on an opposite second end wherein the annular flange is secured to the annular recess and the urging surface is secured to the latching surface; and
 a swab head passing through the axial hole of the connection member and comprising an annular protrusion on a bottom, the annular protrusion extending outward from an end opposite to the ring-shaped projection.

2. The wand applicator of claim 1, wherein the positioning hole includes a cavity on a bottom, and the annular protrusion is partially disposed in the cavity.

3. The wand applicator of claim 1, wherein a diameter of the annular protrusion is greater than that of the axial hole.

4. The wand applicator of claim 1, wherein the second end of the shaft is provided with an attaching member which is configured to fasten in a cap of a cosmetic container.

5. The wand applicator of claim 1, wherein the second end of the shaft is provided with a positioning member.

6. The wand applicator of claim 1, wherein the swab head is formed of nitrile butadiene rubber (NBR) sponge.

7. The wand applicator of claim 1, wherein the swab head is shaped as a sphere, an ellipsoid, or a raindrop.

* * * * *